United States Patent
McEwan et al.

(10) Patent No.: US 6,235,895 B1
(45) Date of Patent: May 22, 2001

(54) METALLO-PORPHYRINS

(75) Inventors: Kenneth J McEwan, Malvern; Harry Anderson, Oxford, both of (GB)

(73) Assignee: The Secretary of State for Defence, Hampshire (GB)

( * ) Notice: Subject to any disclaimer, the term of this patent is extended or adjusted under 35 U.S.C. 154(b) by 0 days.

(21) Appl. No.: 09/230,524

(22) PCT Filed: Jul. 29, 1997

(86) PCT No.: PCT/GB97/02040

§ 371 Date: Dec. 22, 1999

§ 102(e) Date: Dec. 22, 1999

(87) PCT Pub. No.: WO98/05665

PCT Pub. Date: Feb. 12, 1998

(30) Foreign Application Priority Data

Aug. 3, 1996 (GB) .................................................... 9616353

(51) Int. Cl.[7] .................................................... C07F 7/24
(52) U.S. Cl. .................................................... 540/145
(58) Field of Search .............................................. 540/145

(56) References Cited

U.S. PATENT DOCUMENTS 5,871,882 * 2/1999 Schmidhalter ....................... 540/145

FOREIGN PATENT DOCUMENTS

| 94 04614 | 3/1994 | (WO) . |
| 97 27049 | 3/1997 | (WO) . |

OTHER PUBLICATIONS

Anderson H L: "Mesa–alkynylporphyrins" Tetrahedron Lett. (Teleay, 00404039): 92; vol. 33 (8); pp.1101–1104, Univ. Chem. Lab.; Cambridge; CB2 1EW; UK (GB), XP002044362 cited in the application see the whole document.

Beljonne D Et Al: "Investigation of the linear and nonlinear optical response of edge–linked conjugated znc porphyrin oligomers by optical spectroscopy and configuration interaction techniques" J. Chem. Phys. (JCPSA6,00219606);97; vol. 106 (23); pp. 9439–9460, Univ. Mons–Hainaut; Service Chim, Mater. Noureaux, Cent. Recherche Electronique Photonique Moleculaires, Mons; B–7000; Belg. (be), XP002044363 see whole document, especially p. 9444.

S M Lecours Et Al: "Push–Pull Arylethynyl Porphyins." J. Am. Chem Soc. (JACSAT, 00027863); 96; vol. 118 (6); pp. 1497–503, University of Pittsburgh; Department of Chemistry; Pittsburgh; 15260; PA; USA (US), XP002044364.

* cited by examiner

*Primary Examiner*—Robert Gerstl
(74) *Attorney, Agent, or Firm*—Nixon & Vanderhye

(57) ABSTRACT

A compound of formula (I) or (II), wherein: M is Pb or Sn or Bi, n is 1 to 20, each $R^1$ is independently —$SiR_3$ or R or —$CCSiR_3$ or —CCR or H, each $R^2$ is independently —$CCSiR_3$ or —CCR or H, each X is independently H or $C_1$ to $C_{20}$ hydrocarbyl optionally including a carboxylic acid or ester group, each Y is independently H or $C_1$ to $C_{20}$ hydrocarbyl, each R is independently H or $C_1$ to $C_{20}$ hydrocarbyl, Z is $C_1$ to $C_{20}$ alkylene or arylene.

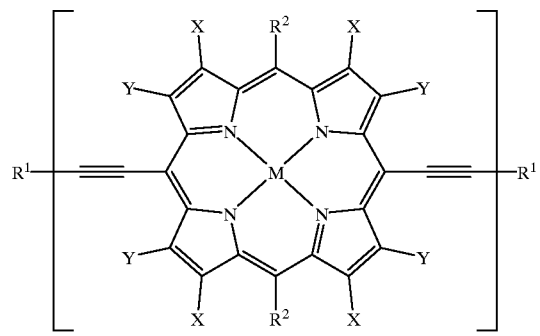

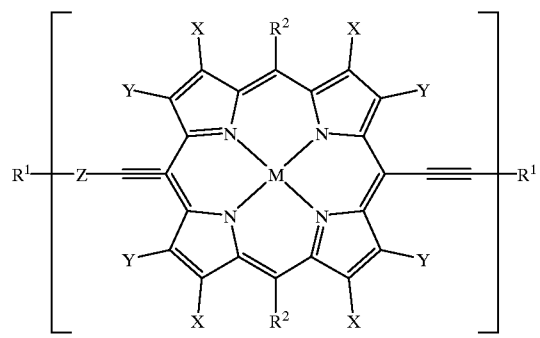

6 Claims, 1 Drawing Sheet

METALLO-PORPHYRINS

This application is a 371 of PCT/GB97/02040 filed Jul. 29, 1997.

It is known that porphyrins with meso-alkynyl substituents have nonlinear optical properties. That is to say, at certain wavelengths, the excited state absorption cross-section $\sigma_{ex}$ of the porphyrin is larger than the ground state absorption cross-section, $\sigma_{gr}$. Therefore the absorption of a sample increases strongly with increasing radiation intensity as the excited state population develops. This property is useful for a variety of electro-optic applications. In addition, the porphyrins described have other important physical properties that make them attractive, they are stable, cheap to produce and are highly soluble in organic solvents. The last property means that they can be used either in a liquid device or in a thin film (e.g. the polymer PMMA).

To be of practical interest, the porphyrin derivative needs to show strong nonlinear absorption properties at wavelengths at or close to those of commonly available lasers, i.e. the ratio $\sigma_{ex}/\sigma_{gr}$ must be large at the specific wavelength of interest. The most commonly used wavelength in the visible region is 532 nm, which corresponds to the frequency doubled wavelength of Nd:YAG, which operates at 1064 nm. Previous studies, by us, on the porphyrin class of materials has shown that the largest excited state absorption coefficient, $\sigma_{ex}(\max)$ occurs at a wavelength slightly longer than that corresponding to the maximum linear absorption, $\sigma_{gr}(\max)$. In the compounds described here we have engineered the structure, through the degree of conjugation and the central metal atom, such that $\sigma_{gr}(\max)$ is at a wavelength slightly less than 532 nm (i.e. typically 500 nm). Most porphyrin compounds exhibit a $\sigma_{gr}(\max)$ at wavelengths significantly less than 500 nm. We have also engineered the molecular structure such that the spectral bandwidth of the linear absorption peak is narrow. This is achieved by designing a rigid and symmetric molecular structure. The narrow bandwidth is crucial since it allows $\sigma_{gr}(\max)$ to be positioned close to 532 nm without drastically increasing the value of $\sigma_{gr}$ at 532 nm. Using these techniques we have been able to maximise the ratio of $\sigma_{ex}/\sigma_{gr}$ at 532 nm.

Having optimised the molecular design and synthesis a number of applications become apparent:

1) The porphyrin sample in either liquid or solid format can be used to change the shape of a Q-switched (nanosecond duration) laser pulse at 532 nm. The tail of the pulse will be severely attenuated as the excited state population accumulates. This will result in a drastic reduction in the laser pulse duration.

2) The energy transmitted through the porphyrin sample in either a liquid or solid format will be reduced, and the reduction will depend on the initial pulse energy. This effect can be used to dampen pulse-to-pulse fluctuations in energy, i.e. the material could be used to stabilise the energy and prevent damage to subsequent optical components.

This invention provides compounds having formula (I) or (II).

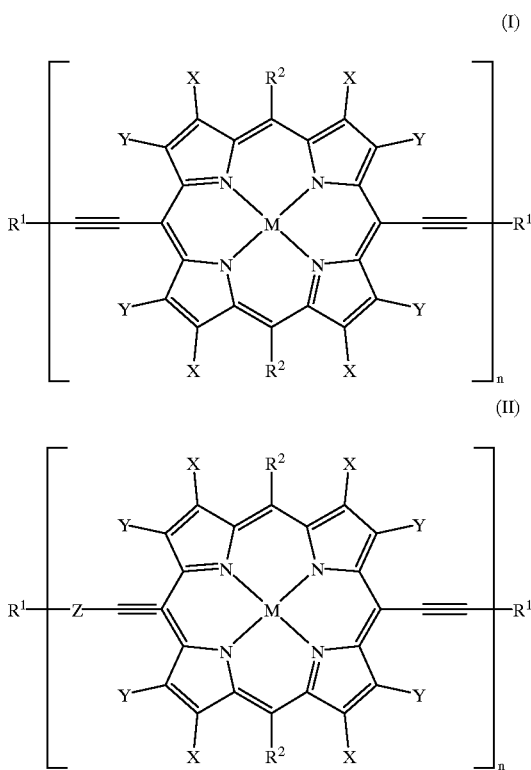

These are monomeric or oligomeric metallo-porphyrin derivatives having meso-alkynl substituents. They are characterised by the fact that the metal atom M is Pb or Sn or Bi. As is demonstrated in the experimental section below, Pb has the effect, compared to the underivatised H form of the porphyrin, of increasing an absorption wavelength by some 40–50 nm. This increase is technically important. It is expected that Sn and Bi will show the same effect.

Substituents are possible on any or all of the twelve ring carbon atoms. The following references describe porphyrins with various ring substituents:

1. Meso-alkynyl porphyrins, H L Anderson, Tetrahedron Lett. 1992, 33, 1101–1103.
2. Conjugated porphyrin ladders, H L Anderson, Inorg. Chem. 1994, 33, 972–981.
3. Synthesis and third order nonlinear optical properties of a conjugated porphyrin polymer, H L Anderson, S J Martin and D D C Bradley, Angew. Chem. Int. Ed/. Engi, 1994, 33, 655–657.
4. Photophysical and transport properties of a novel soluble conjugated polymer based on zinc-porphyrin units edge-linked with acetylenic spacers, K Pichler, H L Anderson, D D C Bradley, R H Friend, P J Hamer, M G Harrison, C P Jarrett, S J Martin and J A Stephens, Mol. Cryst. Liq. Cryst. 1994, 256, 414–422.
5. Supramolecular orientation of conjugated porphyrin oligomers in stretched polymers, H L Anderson, Adv. Mater. 1994, 6, 834–836.
6. Assembly and crystal structure of a photoactive array of five porphyrins, S Anderson, H L Anderson, A Bashall, M McPartlin and J K M Sanders, Angew. Chem. Int. Ed. Engl. 1995, 34, 1096–1099.
7. Femtosecond transient photoinduced transmission measurements on a novel conjugated zinc porphyrin system, G E O'Keefe, G J Denton, E J Harvey, R T Phillips, R H Friend and H L Anderson, J. Chem. Phys. 1996, 104, 805–811.

8. WO 94/04614 (The Trustees of the University of Pennsylvania).

Unsaturated ring substituents may be chosen to make the compound rigid and flat or other desired shape; or to enlarge or modify the conjugated unsaturation system; and thereby to modify the absorption wavelengths. Saturated substituents may be chosen to promote stability or solubility in desired organic solvents or in plastics materials. The knowledge in the art is sufficient to enable a skilled reader to play about with ring substituents in this way. So the following indications are intended to be guidelines rather than rigid definitions.

The compounds are shown as monomers (when n=1) and also as oligomers (when n=2–20). Skilled workers in the field are able to make porphyrin monomers and to join them into chains and rings and networks. These oligomers may have altered and beneficial non-linear absorption properties.

The indications are:

each $R^1$ is independently —$SiR_3$ or R or —$CCSiR_3$ or —CCR or H, each $R^2$ is independently —$CCSiR_3$ or —CCR or H, each X is independently H or $C_1$ to $C_2$, hydrocarbyl optionally including a carboxylic acid or ester group, each Y is independently H or $C_1$ to $C_{20}$ hydrocarbyl, each R is independently H or $C_1$ to $C_{20}$ hydrocarbyl, Z is $C_1$ to $C_{20}$ alkylene or arylene.

The following examples illustrate the invention and are described with reference to reaction schemes 1, 2, 3 and 4.

The compounds may be electrically neutral or cationic or anionic. The nature of any counter-ion is not material to the invention.

EXAMPLE 1

Experimental Details for Preparation of Lead and Tin Porphyrins

4-Butyl-(trimethylsilylethynyl)benzene (2)

Trimethylsilylacetylene (3.6 ml, 26 mmol) was added to an oxygen-free mixture of 4-bromo-butylbenzene 1 (5.0 g, 24 mmol), $Pd(OAc)_2$ (105 mg, 470 µmol.), $PPh_3$ (246 mg, 940 µmol) and CuI (45 mg, 235 µmol) in triethylamine (10 ml) under nitrogen. The mixture was refluxed for 5 h and the triethylamine hydrogen bromide and colloidal palladium produced removed by flash-chromatography ($SiO_2$/60–80 pet. ether). The product was distilled at reduced pressure; unreacted 4-bromo-butylbenzene came over at 44–50° C./0.15 mmHg (yield 1.0 ml) and the product was collected at 73–83° C./0.20 mmHg. Yield 3.094 g (57% or 77% based on recovered starting material). ρ 0.876 g/ml; $δ_H$($CDCl_3$, 200 MHz) 7.40 (2H, d, J=8 Hz), 7.13 (2H, d, J=8 Hz), 2.62 (2H, t), 1.60 (2H, m), 1.35 (2H, m), 0.93 (3H, t), 0.26 (9H, s); $δ_c$($CDCl_3$, 50 MHz) 143.8, 132.1,128.5,120.4,105.6, 93.3, 35.5, 33.3, 22.2,13.8, –6.9; m/z (GCMS, EI) 231.

4-Butylphenylpropynal (3)

A solution of MeLi.LiBr (1.5M in $Et_2O$; 6.25 ml, 9.38 mmol) was added to an oxygen-free solution of 4-butyl-(trimethylsilylethynyl)benzene 2 (2.3 ml, 9.4 mmol) in tetrahydrofuran (10 ml) under $N_2$. After 2 h the mixture was cooled to –25° C. and dry N,N-dimethylformamide (2.0 ml, 26 mmol) was added. The mixture was stirred for 1 h then poured onto 5% aqueous $H_2SO_4$ (150 ml) at 0° C. The product was extracted with dichloromethane, dried over $MgSO_4$ and distilled under reduced pressure collecting the fraction boiling at 81–93° C. at 0.15 mmHg. Yield 1.1789 (67%). ρ 0.947 g/ml; $δ_H$($CDCl_3$, 200 MHz) 9.44 (1H, s), 7.54 (2H, d, J=8.2 Hz), 7.24 (2H, d, J=8.2 Hz), 2.66 (2H, t), 1.60 (2H, m), 1.36 (2H, m), 0.94 (3H, t); $δ_c$($CDCl_3$, 50 MHz) 177.2, 147.4,133.6, 129.1,127.4, 117.0,105.2, 35.7, 33.1, 22.2,13.6; m/z (GCMS, EI) 186.

5,10,15,20-Tetra(trimethylsilylethynyl)porphyin Lead(II) (9)

A solution of 5,10,15,20-tetra(trmethylsilylethynyl) porphyin 8 (48 mg, 69 µmol) in chloroform (5 ml) was added to a solution of lead(II)acetate trihydrate (0.50 g, 1.3 mmol) in pyridine (5 ml). The mixture was refluxed for 1 h, then cooled and diluted with methanol (40 ml) to precipitate the porphyrin. The product was filtered off, washed with methanol and dried under vacuum. Yield 55 mg (89%). $δ_H$H($CDCl_3$, 200 MHz) 9.70 (8H, s), 0.66 (36H, s); $λ_{max}$ ($CH_2Cl_2$)/nm (log ε) 331 (4.30), 378 (4.58), 472 (4.51), 499 (5.46), 658 (3.94), 716 (4.51); m/z (FAB) 900.2 ($C_{40}H_{44}Si_4N_4Pb$ requires 900.24).

5,10,15,20-Tetra(4-butlyphenyl))porphyin (6)

Boron trifluoride etherate (40 µl, 325 µmol) was added to an oxygen-free solution of 4-butlyphenylpropynal 3 (500 µl, 2.5 mmol) and pyrrole (175 µl, 2.5 mmol) in dichloromethane (50 ml) under nitrogen at –33° C. After 3 h the mixture was allowed to warm to room temperature overnight. 2,3-Dichloro-5,6-dicyano-1,2-benzoquinone (431 mg, 1.88 mmol) was added and the product was purified by flash chromatography ($SiO_2$/$CH_2Cl_2$) and recrystallised from dichoromethane/methanol. Yield 114 mg (19%). $δ_H$H ($CDCl_3$, 200 MHz) 8.94 (8H, s), 7.91 (8H, d, J=7.7), 7.37 (8H, d, J=7.7 Hz), 2.81 (8H, t), 1.81 (8H, m), 1.54 (8H, m), 1.10 (12H, t), –4.09 (2H, s); $δ_c$($CDCl_3$) 143.6, 131.8, 128.7, 121.3, 101.5, 97.3, 90.9, 35.9, 33.6, 22.5, 14.1; $λ_{max}$ ($CH_2Cl_2$)/nm (log ε) 309 (4.48), 469 (5.61), 642 (4.83), 737 (4.37); m/z (FAB) 934.4 ($C_{68}H_{62}N_4$ requires 934.50).

5,10,15,20-Tetra(4butlyphenyl)porphyin Lead(II) (10)

A solution of 5,10,15,20tetra(4-butylphenyl)porphyin 6 (41 mg, 44 mmol) in chloroform (5 ml) was added to a solution of lead(II)acetate trihydrate (0.50 g, 1.3 mmol) in pyridine (5 ml). The mixture was refluxed for 1 h, then cooled and diluted with methanol (40 ml) to precipitate the porphyrin. The brown-red crystals were filtered off, washed with methanol and dried under vacuum. Yield 39 mg (77%). $δ_H$($CDCl_3$, 200 MHz) 9.61 (8H, s), 7.99 (8H, d, J=11 Hz), 7.42 (8H, d, J=11 Hz), 2.81 (8H, t), 1.78 (8H, m), 1.55 (8H, m), 1.06 (12H, t); $λ_{max}$ ($CH_2Cl_2$)/nm (log ε) 334 (4.72), 390 (4.77), 483 (4.73), 510 (5.61), 685 (4.19),748 (4.88); m/z (FAB) 1140 ($C_{68}H_{80}N_4Pb$ requires 1140.46).

Triisopropylsilypropynal (5)

Butyl lithium (1.6M in hexanes; 14 ml, 23 mmol) was added to a solution of triisoproplyacetylene 4 (5.0 ml, 23 mmol) in tetrahydrofuran (50 ml) at 0° C. under nitrogen. After stirring for 30 min at 0° C. for 30 min, N,N-dimethylformamide (1.85 ml, 24 mmol) was added. The mixture was allowed to warm to room temperature over 1h then refluxed for 1.5 h, cooled to room temperature and poured into 5% aqueous sulphuric acid. The product was extracted with dichloromethane (3×100 ml) and dried over $MgSO_4$ and purified by column chromatography ($SiO_2$/60–80 pet. ether) and distillation, collecting the fraction 40–45° C./0.15 mmHg. Yield 2.25 g (47%). ρ 0.937 9 /ml; $δ_H$(200 MHz, $CDCl_3$) 9.20 (1H, s),1.09 (21H, m); $δ_c$(50 MHz, $CDCl_3$) 176.8,104.6,100.6,18.2,10.7.

5,10,15,20-Tetra(triisopropylsilylethynyl)porphyin (7)

Boron trifluorde etherate (40 µl, 325 µmol) was added to a degassed solution of triisopropylsilypropynal 5 (561 µl, 2.5 mmol) and pyrrole (175 μl, 2.5 mmol) in dichloromethane (50 ml) under N$_2$. After 3 h, 2,3dichloro-5,6-dicyano-1,2-benzoquinone (431 mg, 1.88 mmol) was added and the product was purified by flash chromatography (SiO$_2$CH$_2$Cl$_2$) and recrystallised from dichloromethane/ methanol. Yield 106 mg (16%). δ$_H$(200 MHz, CDCl$_3$) 9.59 (8H, s), 1.49 (84H$_1$ m), −1.77 (2H, s); δ$_c$(125 MHz, CDCl$_3$) 107.8,102.6, 100.3,19.2,12.0 (+2 resonances too broad to measure reliably); λ$_{max}$ (CH$_2$Cl$_2$)/nm (log ε) 331 (4.37), 454 (5.47), 522 (4.26), 570 (4.33), 6.11 (4.72), 668 (4.34), 713 (4.28).

5,10,15,20-Tetra(triisopropylsilylethynyl)porphyin Lead (II) (11)

5,10,15,20-tetra(triisopropylsilylethynyl)porphyin 7 (25 mg, 24 μmol) and lead(II)acetate trihydrate (0.30 g, 0.79 mmol) were refluxed with pyridine (5 ml) for 30 min. The pyridine was then distilled off and the residue was dissolved in dichloromethane (3 ml), filtered and diluted with methanol (30 ml) to precipitate the product. Yield 20 mg (66%). δ$_H$ (200 MHz, CDCl$_3$): 9.7 (8H, s), 1.51 (84H, m); λ$_{max}$ (CH$_2$Cl$_2$)/nm (log ε) 381 (4.54), 473 (4.54), 500 (5.30), 610 (4.05), 666 (4.32), 719 (4.46).

5,10,15–20-Tetra(trimethylsilylethynyl)porphyin tin (IV) dichloride (12)

5,10,15–20-tetra(trimethylsilylethynyl)porphyin (25 mg, 36.0 μmol) and tin (II) chloride (250 mg, 1.32 mmol) were refluxed with pyridine (8 ml) for 1.5 hours. The pyridine was then distilled off and the residue was dissolved in ethyl acetate (15 ml), filtered and the solvent removed. The product was dissolved in hot 60–80 petroleum ether and filtered again to remove any residual tin salts. The solution was evaporated to dryness to yield the product. Yield 18.9 mg (60.5%). δ$_H$ (200 MHz, CDCl$_3$): 9.92 (8H, s), 0.68 (36H, s); ν$_{max}$/cm$^{-1}$ 2143 (acetylene), 1251 (C-Si); λ$_{max}$ (CH$_2$Cl$_2$)/ nm (log ε) 335 (3.97), 452 (5.20), 600 (3.67), 655 (4.14).

5,10,15–20-Tetra(4-butylphenylethynyl))porphyin tin (IV) dichloride (13)

A solution of 5,10,15–20-Tetra(4-butylphenylethynyl)) porphyin (30 mg, 32.1 μmol) and tin (II) chloride (300 mg, 1.58 mmol) were refluxed with pyridine (5 ml) for 2 hours. The pyridine was then distilled off and the residue was dissolved in ethyl acetate (15 ml), filtered and the solution reduced to a small volume (circa 5 ml). The product was crystallised by addition of 60–80 petroleum ether (30 ml). Yield 8.3 mg (23.1%). δ$_H$ (200 MHz, CDCl$_3$): 9.79 (8H, s), 7.91 (8H, d, J=7.4 Hz), 7.45 (8H, d, J=7.4 Hz), 2.78 (8H, t), 1.74 (8H, m), 1.04 (12H, t); ν$_{max}$/cm$^{-1}$ 2193 (acetylene); λ$_{max}$(CH$_2$Cl$_2$)/nm (log ε) 326 (4.31), 470 (5.13), 672 (4.35).

Scheme 1

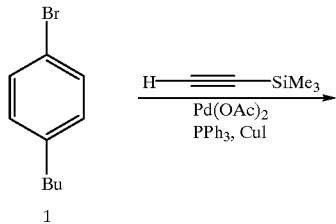

Scheme 2

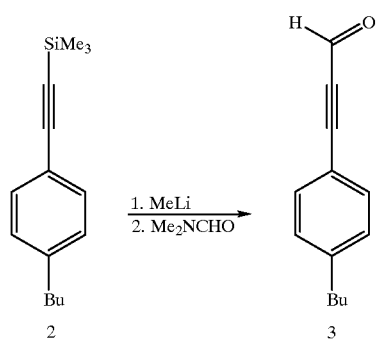

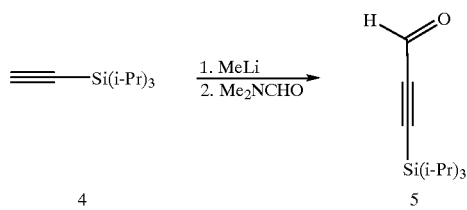

Scheme 3

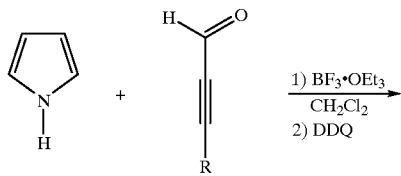

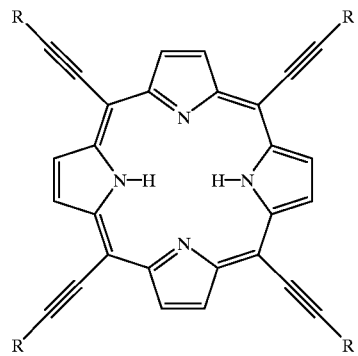

6 TnBuBAP(H$_2$): R = p-C$_6$H$_4$Bu (20%)
7 TTIPSAP(H$_2$): R = Si(i-Pr)$_3$ (16%)

Scheme 4

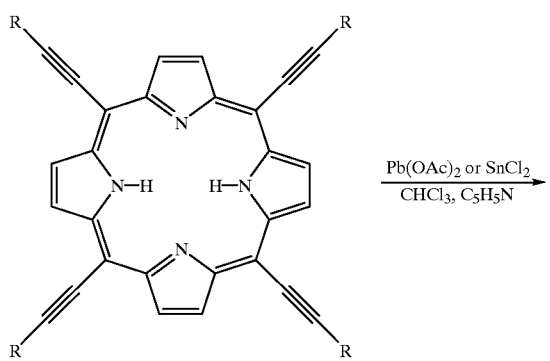

6 TnBuBAP(H$_2$): R = p-C$_6$H$_4$Bu
7 TTIPSAP(H$_2$): R = Si(i-Pr)$_3$
8 TTMSSAP(H$_2$): R = SiMe$_3$

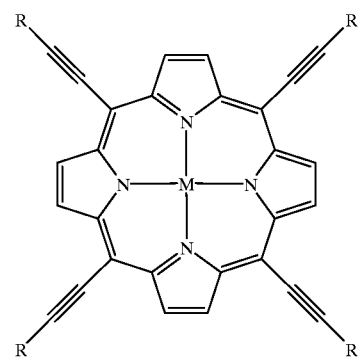

9 TTMSAP(Pb): M = Pb, R = SiMe$_3$ (89%)
10 TnBuBAP(Pb): M= Pb, R = p-C$_6$H$_4$Bu (77%)
11 TTIPSAP(Pb): M = Pb, R = Si(iPr)$_3$ (66%)
12 TTMSAP(SnCl$_2$): M = SnCl$_2$, R = SiMe$_3$
13 TnBuBAP(SnCl$_2$): M = SnCl$_2$, R = p-C$_6$H$_4$Bu

BRIEF DESCRIPTION OF DRAWINGS

EXAMPLE 2

Figure 1:
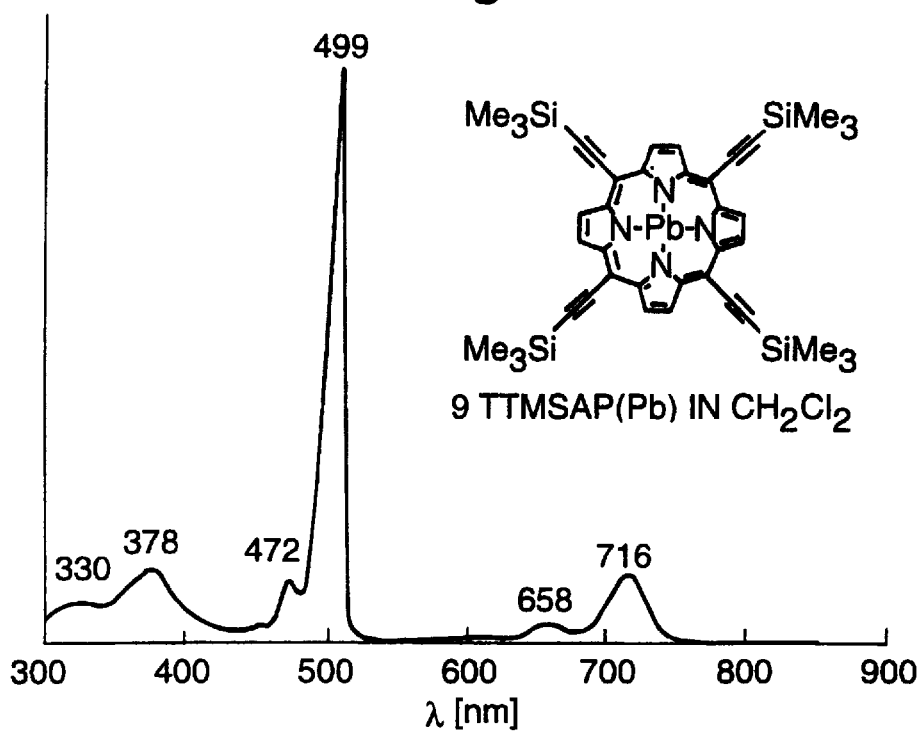
Figure 2:
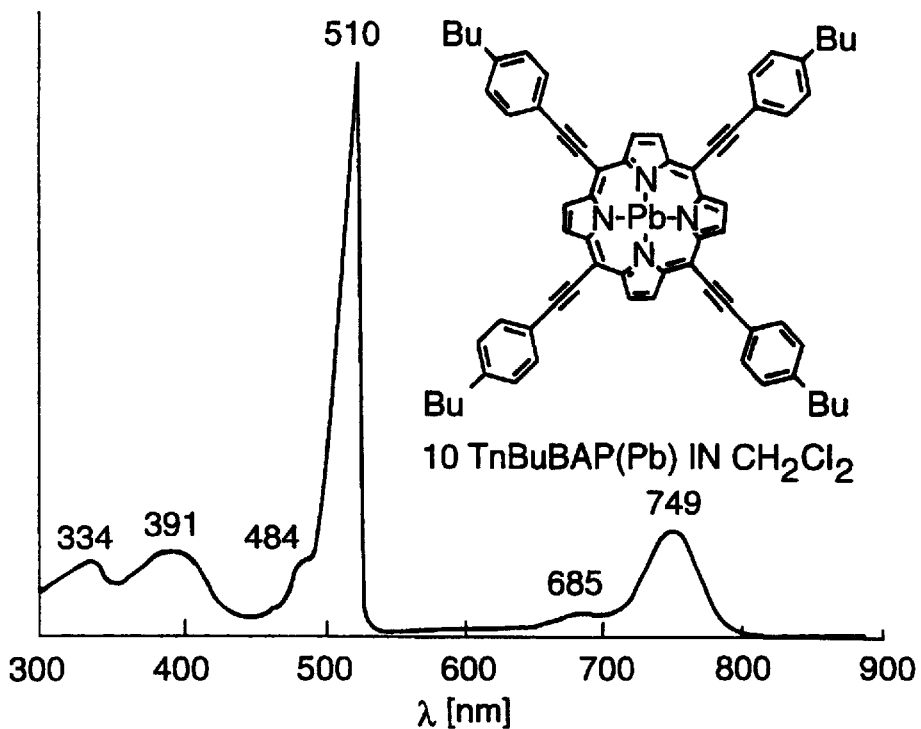

UV-visible spectra were obtained of compounds 9 and 10, and these are shown in the accompanying FIGS. 1 and 2. These absorption figures are contrasted with those obtained from the unsubstituted hydrogen homologues 6 and 8, and also with the zinc homologues, in the following table. All results were obtained with the porphyrin derivatives dissolved in methylene dichloride:

|          |           | Visible Absorption Maxima (nm) | |
|----------|-----------|---------|-------------------------|
| Compound | Ring Atom | (Major) | (Minor)                 |
| 9        | Pb        | 499     | (378) (472) (658) (716) |
| 8        | H$_2$     | 452     | (568) (607) (647)       |
|          | Zn        | 461     | (437) (606) (654)       |
| 10       | Pb        | 510     | (749)                   |
| 6        | H$_2$     | 469     | (642) (737)             |
|          | Zn        | 478     | (681)                   |

It can be seen that lead has a much more dramatic action than does zinc in increasing the major visible absorption maximum of each porphyrin compound.

EXAMPLE 3

In continuing work, the compounds 14, 15, 16 and 17 below will be synthesised. Structures such as the tetra-anthracene porphyrin 15 and the anthracene-linked polymer 16 are expected to be more conjugated that their phenyl analogues, and when the anthracene chromophores are excited they should transfer energy to the porphyrins. In these structures, R may be H or alkyl. Long aliphatic side chains will make the porphyrins highly soluble in organic solvents, which facilitate preparation of thin film samples and also gives materials with good stability.

Porphyrins such as 17 are expected to have extremely red-shifted absorption spectra and to be very polarisable, due to the contribution of dipolar resonance forms such as 18.

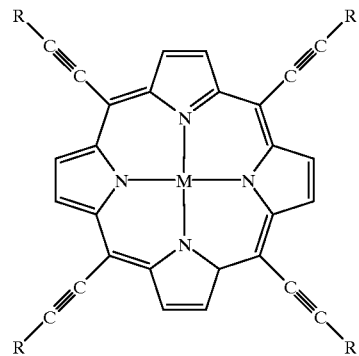

14

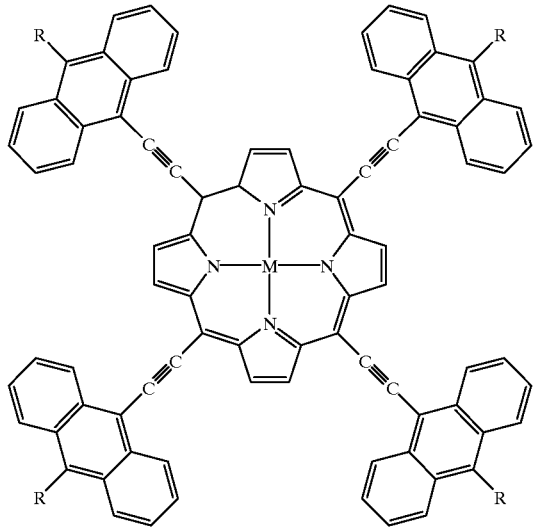

15

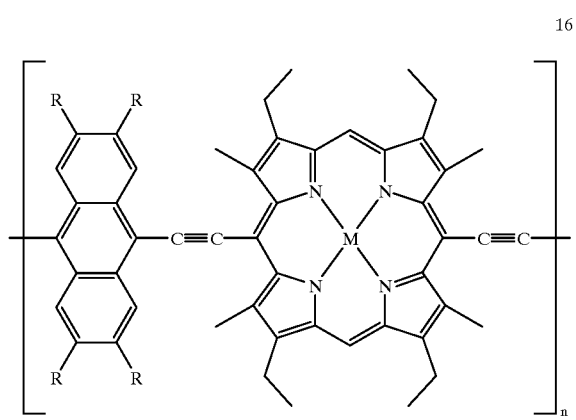
16
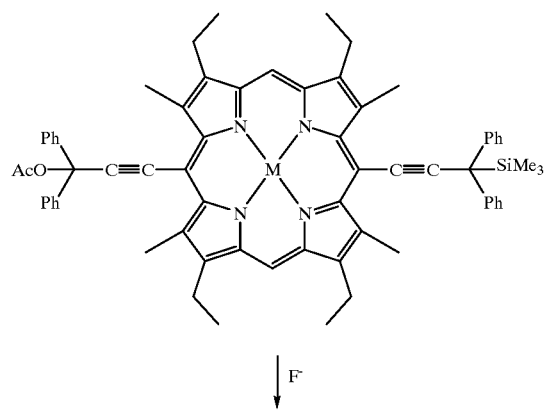
12b
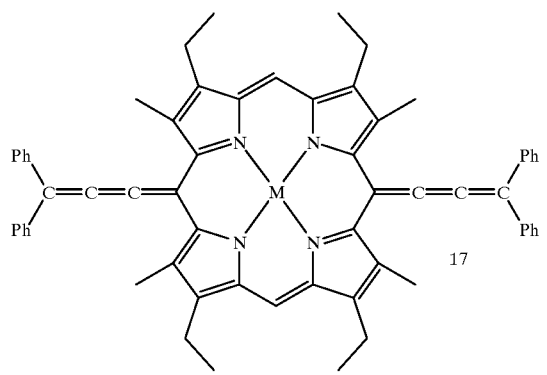
17
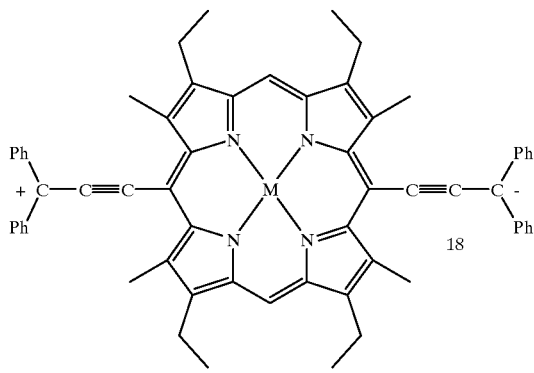
18
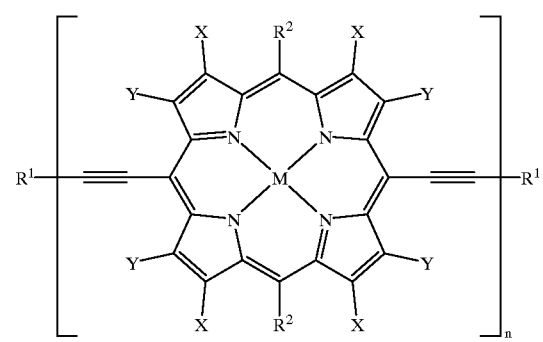
(I)
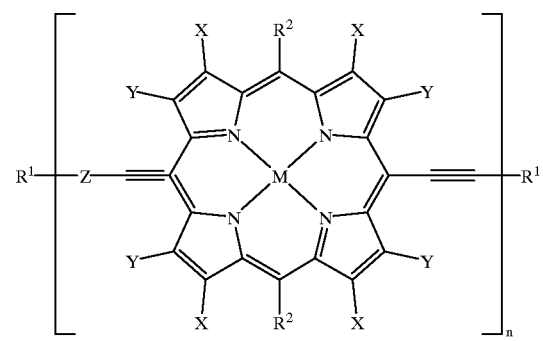
(II)
What is claimed is:
1. A compound of the formula (I) or (II) wherein:
M is Pb or Sn or Bi,
n is 1 to 20,
each $R^1$ is independently —$SiR_3$ or R or —C≡C$SiR_3$ or —C≡CR or H, each $R^2$ is independently —C≡CSiR$_3$ or —C≡CR or H, each X is independently H or $C_{12}$ to $C_{20}$ hydrocarbyl optionally including a carboxylic acid or ester group, each Y is independently H or $C_1$ to $C_{20}$ hydrocarbyl, each R is independently H or $C_1$ to $C_{20}$ hydrocarbyl, Z is $C_1$ to $C_{20}$ alkylene or arylene.

2. A compound of formula (I) as claimed in claim 1, wherein n is 1 each $R^1$ is —SiR$_3$ or R each $R^2$ is C≡CSiR$_3$ or —C≡CR each X is H each Y is H each R is $C_1$–$C_5$ alkyl or alkaryl.

3. A compound as claimed in claim 2, wherein:

each $R^1$ is —SiR$_3$ each $R^2$ is C≡CSiR$_3$ each R is $C_1$–$C_3$ allyl.

4. A compound as claimed in claim 2, wherein:

each $R^1$ is R each $R^2$ is C≡CR each R is $C_7$–$C_{12}$ alkaryl.

5. A compound as claimed in claim 1, wherein:

n is 1 to 12, each $R^1$ is C≡CSiR$_3$ or —C≡CR each $R^2$ is H each X is $C_1$–$C_{20}$ hydrocarbyl optionally including a carboxylic acid or ester group each Y is $C_1$–$C_3$ alkyl each R is $C_1$–$C_3$ alkyl or $C_7$–$C_{12}$ alkaryl each Z is arylene.

6. A compound as claimed in claim 1, wherein M is Pb.

* * * * *